(12) United States Patent
Pyhälahti

(10) Patent No.: US 7,601,880 B2
(45) Date of Patent: Oct. 13, 2009

(54) METHOD FOR CATALYTIC DEOXYGENATION OF PROCESS FLUIDS OF OLEFIN DIMERIZATION PROCESS

(75) Inventor: Antti Pyhälahti, Helsinki (FI)

(73) Assignee: Neste Oil Oyj, Espoo (FI)

( * ) Notice: Subject to any disclaimer, the term of this patent is extended or adjusted under 35 U.S.C. 154(b) by 181 days.

(21) Appl. No.: 10/572,384

(22) PCT Filed: Sep. 17, 2004

(86) PCT No.: PCT/FI2004/000544

§ 371 (c)(1),
(2), (4) Date: Mar. 16, 2006

(87) PCT Pub. No.: WO2005/026084

PCT Pub. Date: Mar. 24, 2005

(65) Prior Publication Data

US 2007/0100194 A1    May 3, 2007

Related U.S. Application Data

(60) Provisional application No. 60/504,247, filed on Sep. 18, 2003.

(51) Int. Cl.
*C07C 1/00* (2006.01)
*C07C 41/01* (2006.01)
(52) U.S. Cl. .................. 585/733; 568/694; 568/697; 568/895; 568/904
(58) Field of Classification Search .......... None
See application file for complete search history.

(56) References Cited

U.S. PATENT DOCUMENTS

| 4,423,271 | A  | 12/1983 | Obenaus et al. |
| 4,629,710 | A  | 12/1986 | Smith, Jr. |
| 5,043,519 | A  | 8/1991  | Orfeo et al. |
| 5,095,164 | A  | 3/1992  | Gabel et al. |
| 5,336,841 | A  | 8/1994  | Adams |
| 5,849,971 | A  | 12/1998 | Sakuth et al. |
| 6,028,239 | A  | 2/2000  | Marion et al. |
| 6,156,947 | A  | 12/2000 | Vora |
| 6,548,721 | B1 | 4/2003  | Mc Culloch et al. |

FOREIGN PATENT DOCUMENTS

| DE | 3612444 A1    | 10/1987 |
| EP | 0 712 824 A1  | 5/1996  |
| GB | 2 325 237 A   | 11/1998 |
| WO | WO-02/36528 A1 | 5/2002 |

*Primary Examiner*—Rosalynd Keys
(74) *Attorney, Agent, or Firm*—Birch, Stewart, Kolasch & Birch, LLP (57) ABSTRACT

The present invention relates to a method for catalytic deoxygenation of process fluids of olefin dimerization processes. According to the invention at least one process fluid containing oxygenates is brought into contact with a deoxygenation catalyst at, at least one location in a column or connected to a column. The present invention relates also to a process for dimerization of olefins, wherein at least part of olefin feed is dimerized in at least one dimerization reaction zone to produce a first product stream comprising oxygenates, and separating in a distillation zone, comprising one or more distillation columns, the first product stream into a second product stream and a third product stream and at, at least one location of the distillation column or a vessel connected to the distillation column is located a deoxygenation catalyst for decomposing oxygenates.

8 Claims, 7 Drawing Sheets

METHOD FOR CATALYTIC DEOXYGENATION OF PROCESS FLUIDS OF OLEFIN DIMERIZATION PROCESS

This application is the National Phase of PCT application PCT/FI2004/000544, filed Sep. 17, 2004 and claims priority under 35 U.S.C. 119(e) on U.S. Provisional Application Nos. 60/504,247 filed Sep. 18, 2003, all of which are hereby incorporated by reference.

FIELD OF INVENTION

The present invention relates to a method for catalytic deoxygenation of process fluids of olefin dimerization processes. Particularly the invention relates to the removing of oxygenates from the process fluids.

STATE OF THE ART

When olefins and particularly isoolefins are dimerized in the presence of acidic catalysts, the progress of the oligomerization reaction needs to be limited to the dimer stage. High dimer selectivity is achieved by adding suitable polar components to the reaction mixture. Typically oxygenates, such as water, primary, secondary and tertiary alcohols and ethers are used as the polar components. The control of dimer selectivity with oxygenates works well, but the presence of oxygenates makes certain side reactions possible.

According to the results of tests performed by the applicant wherein isobutene, isoamylenes and other reactive olefins are dimerized in the presence of water and alcohols with an acidic catalyst, the olefins present in the reaction mixture form alcohols with water, and the alcohols may react with olefins to ethers.

When a mixture of C4 and C5 olefins is dimerized in the presence of water/TBA moderator with an acidic catalyst, the following side reactions typically take place.

Such reactions are formation reactions of oxygenates. Please note that this list is not exhaustive, the actual number of possible reactions is much higher:

isobutene+$H_2O$ ↔tert-butyl-alcohol (TBA)
1-butene+$H_2O$ ↔1-butanol
1-butene+$H_2O$ ↔2-butanol
c-2-butene+$H_2O$ ↔2-butanol
t-2-butene+$H_2O$ ↔2-butanol
1-butanol+isobutene ↔n-butyl-tert-butyl-ether
2-butanol+isobutene ↔sec-butyl-tert-butyl-ether
2-butanol+2-butene ↔di-sec-butyl-butyl-ether
isoamylene+$H_2O$ ↔tert-amyl-alcohol The amount of ethers formed this way is not very high because the amount of linear butenes is limited and the equilibrium constant for formation of the heavy ethers is low.

In the case the dimerization is performed using primary alcohol like methanol and ethanol instead of water or TBA as the oxygenate feedstock, the potential side reactions, i.e. formation reactions of oxygenates are different. A few examples are presented below:

isobutene+methanol ↔methyl-sec-tert-butyl-ether (MTBE)
2-butene+methanol ↔methyl-sec-butyl-ether (MSBE)
isobutene+ethanol ↔ethyl-sec-tert-butyl-ether (ETBE)
2-butene+ethanol ↔ethyl-sec-butyl-ether (ESBE)
isooctene+methanol ↔methyl-iso-octyl-ether
isooctene+ethanol ↔ethyl-iso-octyl-ether
isoamylene+methanol ↔methyl-tert-amyl-ether
isoamylene+ethanol ↔ethyl-tert-amyl-ether Here it should be noted that the isobutene dimer reacts in some extent to C9 ethers (methyl-iso-octyl-ether), which will follow the dimer product in distillation because boiling points of said ethers are between the boiling points of isobutene dimers and trimers. C5 and C6 ethers can be separated from the product and recycled, but however, they are very abundant in the dimerization reactor effluent and thus their complete removal requires careful operation and significant energy input to distillation.

Although the amount of oxygenates in the dimer product is limited, the presence of oxygenates in the products is a problem. Even if C8 ethers have very low water solubility and they are good gasoline components as such, the negative publicity around MTBE has created a problem for ethers, and thus they should be removed from the final product.

Further treatment of the remaining light hydrocarbons e.g. in an alkylation process requires almost total removal of oxygenates from the stream comprising the remaining unreacted hydrocarbons.

If the dimer product is hydrogenated, oxygenates tend to act as inhibitors in hydrogenation reactions thereby increasing the needed amount of catalyst and requiring more severe conditions.

The decomposition products of alcohols and ethers in hydrogenation are mainly light saturated hydrocarbons and water. Without special measures the light hydrocarbons leave the hydrogenation unit with fuel gas and thus their only value is their heat of combustion, i.e. they mean lost production or they remain in the product increasing its vapor pressure and thereby reducing the market value of the product.

The removing of the oxygenates, especially heavy ethers from the products by distillation is difficult because the boiling points of the heavy ethers are within the same ranges as those of the desired products.

The amount and quality of said side-products depend on the feedstock and process conditions.

Typically, an effluent from an isobutane dehydrogenation process contains 40-50 weight-% of isobutene and approximately 1 weight-% of mixed linear butenes, such as 1-butene, cis-2-butene and trans-2-butene and 0.02-0.15 weight-% of butadiene.

If the feed of the process is a typical refinery C4 stream, it usually contains 10-25 weight-% of isobutene, approximately 30-50 weight-% of linear butenes, 0-5 weight-% of C3 products, 0-5 weight-% of C5 products, the rest consisting mainly of butanes.

Figure 1:
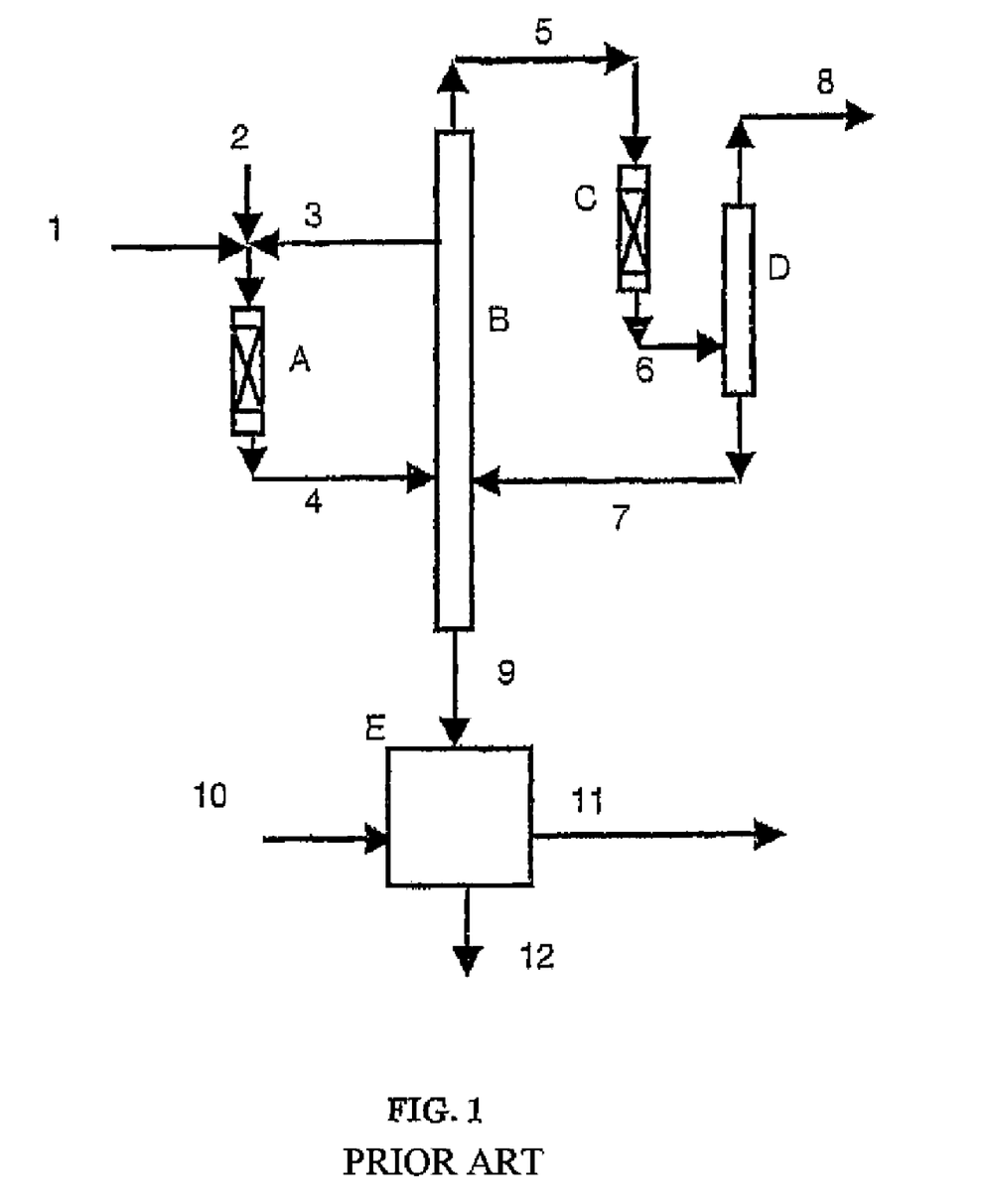
In FIGS. 1 and 2, schematic illustrations of dimerization processes according to the state of the art are described.

FIG. 1 represents a schematic illustration of a typical dimerization process and unit according to the state of the art. Hydrocarbon feed stream 1, oxygenate makeup stream 2 and oxygenate rich recycle stream 3 are combined and fed to the primary dimerization reaction zone A. The effluent 4 from this reaction zone is conducted to the dimer separation column B. The bottom product of this column, stream 9, consists mainly of the produced dimers, higher oligomers and heavy oxygenate side products. The intermediate boiling oxygenates are separated as the recycle stream 3, and the remaining light hydrocarbons as the overhead stream 5. The dimer separation column B overhead stream 5 is conducted to the secondary dimerization reaction zone C where the remaining monomer is dimerized and the effluent 6 of this reaction zone is conducted to the light hydrocarbon separation column D. The purpose of this column is to remove unreacted light hydrocarbons from the system. Thus the overhead product of this column, the stream 8, consist mainly of the non-reacting light hydrocarbons, and the bottom product 7 contains the dimers and heavier oligomers, and other heavy side products and major part of the oxygenates present in the effluent of reaction zone C and optionally some light hydrocarbons. The stream 7 is returned to the dimer separation column B where it is fractionated as was previously described. Further, an optional hydrogenation step E is presented where the olefinic dimer product is hydrogenated to produce the corresponding paraffinic dimer. In this step hydrogen stream 10 and dimer separation column bottom stream 9 are contacted with each other in the presence of a suitable catalyst. The purpose of this step is to saturate the olefinic dimer and heavier oligomers. The excess of hydrogen and possible light decomposition products of hydrogenation step are removed as gas stream 11, typically fuel gas and the saturated dimer product are taken out as stream 12.

Typically there may be approximately 0.1-0.3 weight-% of ethers and alcohols present in the diisobutene product (stream 9 in the process presented in FIG. 1) leaving this type of the dimerization process treating isobutane dehydrogenation effluent.

If the feed of the process is a typical refinery C4 stream, the dimerization process flow scheme is likely different. When said mixture is dimerized, the dimer product contains 1 to 5 weight-% of C8 ethers and alcohols. Thus the amount of the oxygenate side products is much higher than in the dimer produced from the earlier mentioned dehydrogenation effluent.

GB 2 325 237 discloses a process for dimerizing isobutene wherein methanol is used as the moderator. The process scheme is presented in FIG. 2.

Figure 2:
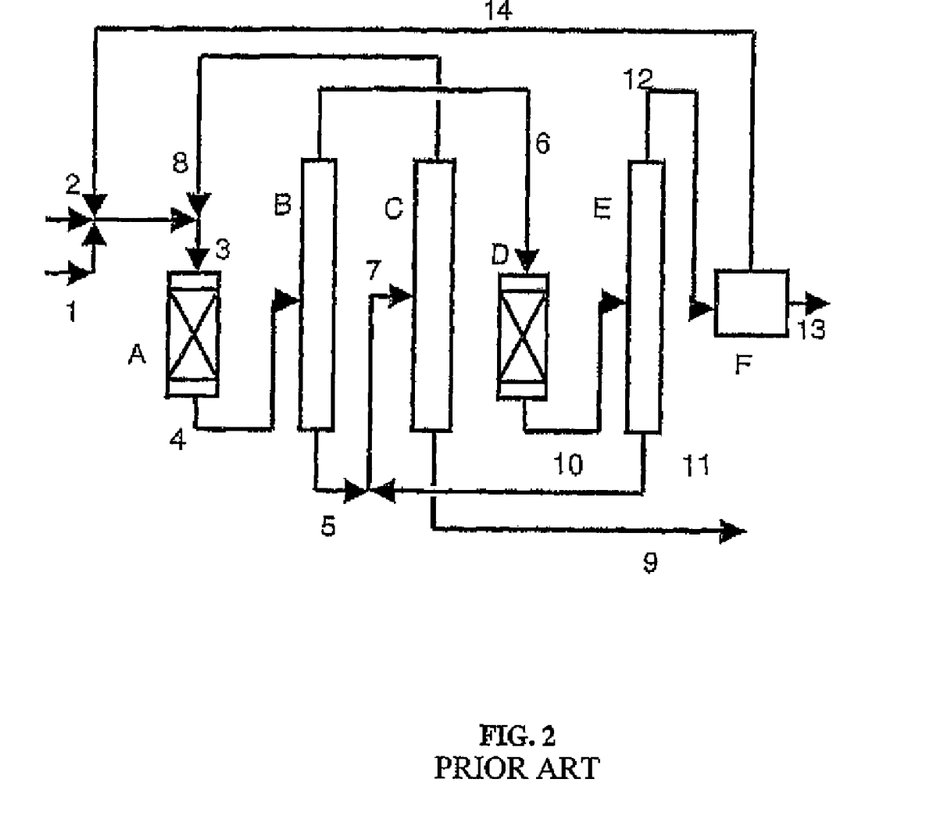

In FIG. 2 hydrocarbon feed to the process (stream 1) is mixed with fresh methanol (stream 2), recovered methanol (stream 14) and recycled oxygenates (stream 8). The combined feed is conducted to the primary reaction stage A, where the hydrocarbons are partially converted to dimer. The effluent (stream 4) of the primary reaction stage A is conducted to a distillation column B where the unreacted light hydrocarbons and at least part of the methanol are separated from the reactor effluent to stream 6. The remaining part of the reactor effluent consisting mainly of dimer and MTBE goes to stream 5. The light hydrocarbons in stream 6 are conducted to a secondary reaction stage D, where more dimer is formed. The effluent 10 from D is conducted further to column E where the unreacted light hydrocarbons are removed from the mixture to stream 12. Stream 12 contains also some methanol. For this reason stream 12 is conducted to methanol recovery stage F, from which the recovered methanol is recycled to the inlet of reactor A via stream 14 and the remaining light hydrocarbons are removed from the process via stream 13. The bottom streams of columns B and E, streams 5 and 11, respectively, containing the major part of the reaction products, are combined to stream 7, which is fed to the dimer separation column C. In the column C the dimer product is separated from MTBE and other light and intermediate boiling components present in stream 7, which are recycled to the primary reaction stage A via stream 8.

According to GB 2 325 237 the feed to the dimer separation column (C in FIG. 2) contains 34.80 weight-% of MTBE and 0.61 weight-% of C9 ethers. In the final dimer product no MTBE is present but C9 ethers are concentrated to 1.03 weight-% (stream 9 in FIG. 2).

Thus, the dimer products obtained from dimerization processes according to the state of the art may contain 0.1 . . . 5 weight-% of ethers, alcohols, acids, ketones and the like and other oxygenates.

Based on the above it can be seen that there exists an evident need for a method for removing the undesired oxygenates from process fluids of olefin dimerization processes.

OBJECT OF THE INVENTION

An object of the invention is a method for catalytic deoxygenation of process fluids of olefin dimerization processes.

A further object of the invention is to provide an improved process for the dimerization of olefins wherein oxygenates are removed.

A still further object of the invention is to improve the quality of process fluids of olefin dimerization processes by removing oxygenates.

Process fluids mean here all oxygenate containing effluents, internal column streams and process streams in olefin dimerization processes.

Oxygenates mean here water, primary, secondary and tertiary alcohols and ethers.

Characteristic features of the methods according to the invention are stated in the claims.

SUMMARY OF THE INVENTION

The present invention relates to a method for catalytic deoxygenation of process fluids of olefin dimerization processes, wherein at least one process fluid containing oxygenates is brought into contact with a suitable catalyst at, at least one selected location of the process. Suitable catalysts are deoxygenation catalysts. The location is preferably in a column or connected to a column.

The present invention relates also to a process for dimerization of olefins, wherein at least part of olefin feed is dimerized in at least one dimerization reaction zone to produce a first product stream comprising oxygenates, and separating in a distillation zone, comprising one or more distillation columns, the first product stream into a second product stream and a third product stream, and at, at least one location of the distillation column or a vessel connected to the distillation column is located a deoxygenation catalyst for decomposition of oxygenates.

DETAILED DESCRIPTION OF THE INVENTION

In general, the formation reactions of oxygenates, such as alcohols (e.g. tert-butanol and sec-butanol) and ethers (e.g. MTBE, tert-butyl-sec-butyl-ether and di-sec-butyl-ether), are exothermal equilibrium reactions, wherein acidic catalyst are needed. Examples of such formation reactions were presented above.

In the method according to the invention for catalytic deoxygenation of process fluids of olefin dimerization processes, at least one process fluid, relatively rich in oxygenates to be decomposed and lean in decomposition products of said oxygenates, is brought into contact with a deoxygenation catalyst at, at least one location in the process. The oxygenates comprise water, primary, secondary and tertiary alcohols and ethers, particularly tert-butyl-alcohol, 1-butanol, 2-butanol, n-butyl-tert-butyl-ether, sec-butyl-tert-butyl-ether, di-sec-butyl-butyl-ether, tert-amyl-alcohol, methyl-tert-butyl-ether, methyl-sec-butyl-ether, ethyl-tert-butyl-ether, ethyl-sec-butyl-ether, methyl-iso-octyl-ether, ethyl-iso-octyl-ether, methyl-tert-amyl-ether and ethyl-tert-amyl-ether.

The location of the catalyst is selected so that oxygenates and their decomposition products are present in such concentrations that the concentration of the oxygenate to be decomposed exceeds the concentration, which would be in reaction equilibrium with the decomposition products under prevailing conditions. As it is evident from the definition of chemical equilibrium, this is the absolute prerequisite for the desired decomposition to take place. Also follows from the principles of chemical thermodynamics, it is obvious that when a location(s) for the catalyst is selected, at least the concentrations of said oxygenate and its decomposition products and temperature and pressure having an effect on the value of the equilibrium constant of the reaction must be taken into account.

Now it has been surprisingly found that in olefin dimerization processes, in the dimerization units and particularly in the distillation columns there are locations wherein these conditions are fulfilled. However, without any catalysts at such locations the decomposition reactions will not take place. In many cases the temperatures of such zones are high thus shifting the equilibrium of the reaction away from unwanted oxygenates. Thus, the decomposition of oxygenates originating from the dimerization process fluids can be efficiently accomplished using suitable catalysts at such locations. Examples of suitable locations for achieving the decomposition of oxygenates are presented in the examples below.

Furthermore, it has been surprisingly found that it is possible to create locations where oxygenates in the process fluids of olefin dimerization processes can be decomposed by adjusting the process conditions (pressure, temperature and compositions of the mixtures) and by placing suitable catalyst in said locations. I.e. it is possible to create zones having a high concentration of oxygenates and low concentration of decomposition products of said oxygenates. In many cases the temperatures of such zones are high thus shifting the equilibrium of the reaction away from unwanted oxygenates.

According to the invention, by incorporating a suitable amount of a suitable catalyst at such locations, oxygenates can be decomposed and thereby removed from the process fluids of olefin dimerization processes very efficiently.

The location of the catalyst depends on the structure of the plant and on the oxygenates to be decomposed and thus examples of different configurations are treated separately in the enclosed figures. In general the location of the catalyst must be such that under the prevailing conditions the concentration of the oxygenates present is higher than that of the thermodynamic equilibrium concentration of the oxygenates to be decomposed. The catalyst is placed in the dimerization units and preferably inside of a column or in a vessel connected to a column. The dimerization process may contain one dimerization unit (dimerization reaction zone) or more than one dimerization units and one or more columns.

In a vessel connected to a column means here that the catalyst is located in a separate vessel, which is connected to the column, and the vessel may be located externally with respect to the column.

The column is preferably a distillation column and the contacting is carried out in a vessel or in a section of the distillation column. The section of the distillation column may comprise less than the total volume of the distillation column, or at least a portion of the lower half of the distillation column, or at least a portion of the upper half of the distillation column, or at least a portion of the center one-half of the distillation column, or at least a portion of the center one-third of the distillation column, or a portion of the lower half of the distillation column and a portion of the upper half of the distillation column.

Typically the thermodynamic conditions in the oxygenate decomposition zones comprise a temperature range of 30-300° C. and a pressure range of 100-5000 kPa.

The invention is illustrated in more detail in the examples of the following FIGS. 3-7. However, the examples are merely illustrative and it is evident to a man skilled in the art that they are not intended to limit the scope of the invention by any means.

Figure 3:
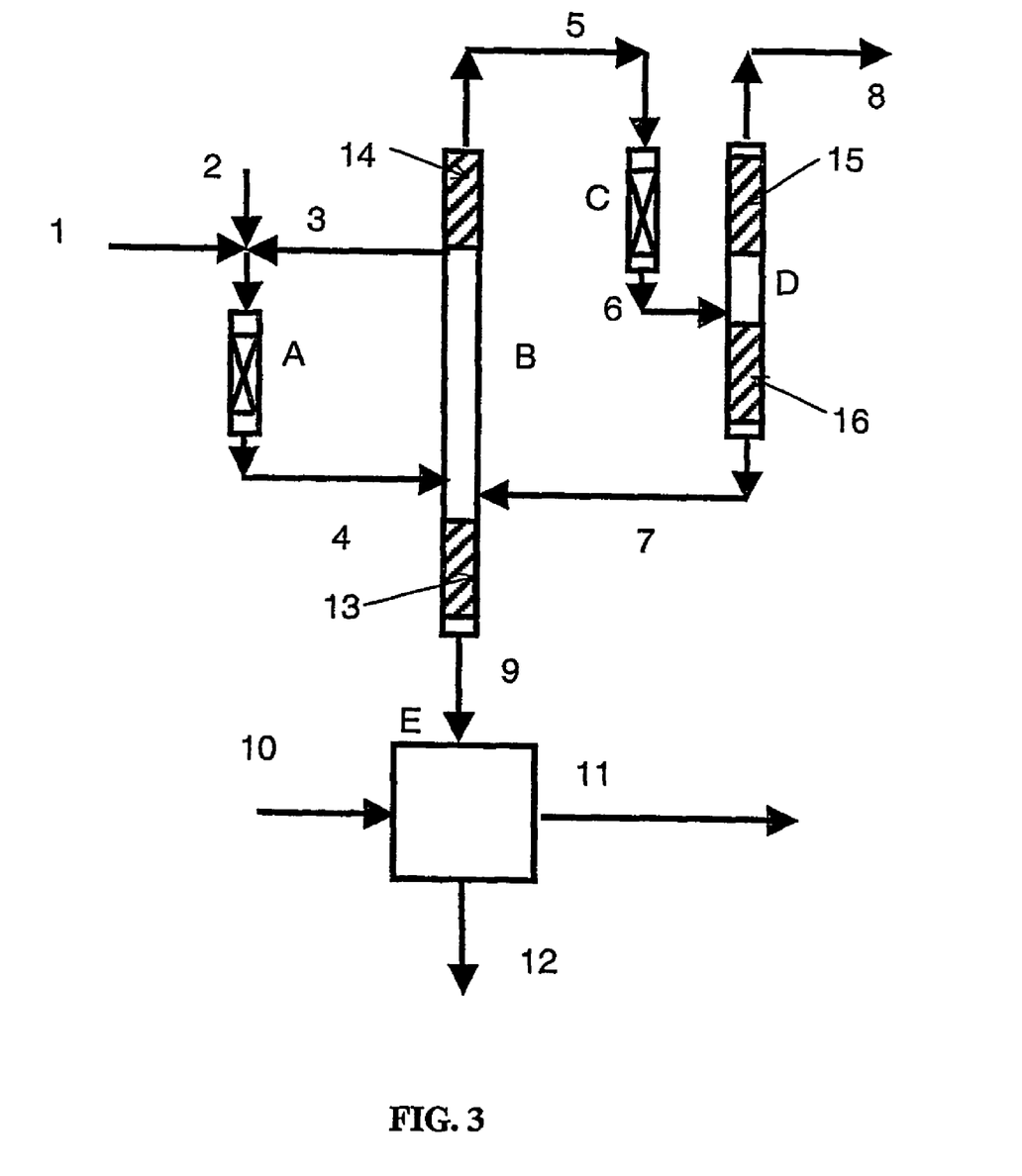
FIG. 3 represents a schematic illustration of a dimerization process similar to the one of FIG. 1, but additionally containing the features of the invention.

In FIG. 3, hydrocarbon feed stream 1, oxygenate makeup stream 2 and oxygenate rich recycle stream 3 are combined and fed to the primary dimerization reaction zone A. The effluent 4 from this reaction zone A is conducted to the dimer separation column B. The bottom product of this column, stream 9, consists mainly of the produced dimers and higher oligomers and heavy oxygenate side products like tert-butyl-sec-butyl-ether and di-sec-butyl-ether. The intermediate boiling oxygenates (e.g. ert-butyl-alcohol) are separated as the recycle stream 3, and the remaining light hydro-carbons as the overhead stream 5. The dimer separation column overhead stream 5 is conducted to the secondary dimerization reaction zone C where the remaining monomer is dimerized and the effluent 6 of this reaction zone C is conducted to the light hydrocarbon separation column D. The overhead product of column D stream 8 consist mainly of the non-reacting light hydrocarbons but there are also traces of oxygenates. The bottom product 7 contains the dimers, heavier oligomers, other heavy side products, major part of the oxygenates present in the effluent of reaction zone C and typically light hydrocarbons as well. Stream 7 is returned to dimer separation column B where it is fractionated as was previously described. In an optional hydrogenation step E hydrogen stream 10 and dieter separation column bottom stream 9 are contacted with each other in the presence of a suitable catalyst. The excess of hydrogen and possible light decomposition products of hydrogenation step are removed as gas stream 11, and the saturated dimer product is taken out as stream 12.

In this plant configuration, a very suitable location for a deoxygenation catalyst is the lower part 13 (oxygenate decomposition zone) of the dimer separation column B of the dimerization process, preferably between the feed point and reboiler (not presented in the figure).

When the dimer separation column B in FIG. 3 is operated in a rational manner i.e. the bottom product consists of dimers and heavier components, water and light hydrocarbons have a very high tendency to move upwards in this part of the column. As a result they are removed from the oxygenate decomposition zone (lower part 13), and equilibrium will not be established, but oxygenates are continuously decomposed before they reach the bottom of the column and thereby get in to the product.

Moreover the temperature at the oxygenate decomposition zone (lower part 13) of the column B is 150-220° C. At this temperature oxygenates are readily decomposed to their constituents, i.e. the equilibrium of the oxygenate formation reactions, examples of which are presented above, is shifted towards the reactants. Thus ethers are converted to olefins and alcohols, and alcohols are converted to olefins and water.

Further, the decomposition reactions of oxygenates are endothermic reactions and thus the reaction zone should preferably be warmed. When the oxygenate decomposition zone is located in a distillation column, this is done by vapor rising from the reboiler without any additional equipment. Especially the di-sec-buty-ether and sec-butyl-tert-butyl-ethers can be advantageously removed this way because their boiling points are near to that of the dimer product and they are difficult to remove from the dimer product by conventional distillation.

In most cases the separation of the decomposition products and warming of the oxygenate decomposition zone can be accomplished without the need to add any new major pieces of equipment or without disturbing the normal operation of the plant.

In FIG. 3 other alternative locations for the catalyst (oxygenate decomposition zone) are shown. Often it is useful to prevent access of excessive amounts of light oxygenates (e.g. tert-butanol in the case of isobutene dimerization) to the subsequent process steps. Besides improving selectivity, oxygenates reduce strongly the activity of dimerization catalysts. Thus it is necessary to reduce the amount of oxygenates to a very low level in order to have high conversion in the relatively diluted olefin feed entering the reactors of the secondary reaction zone C.

By placing the deoxygenation catalyst to the upper end of dimer separation column B, at 14 (oxygenate decomposition zone), the amount of alcohols flowing to the secondary reaction zone C can be reduced by decomposing the alcohols present in column B overhead product to olefin and water. Because the water resulting from the decomposition of alcohols can be separated as free water from the overhead drum of column B, the total oxygenate input to the subsequent process stages can be thereby reduced. Simultaneously the olefin released remains in the hydrocarbon stream and can be dimerized in secondary reaction zone C.

In the same way by placing a suitable catalyst to the top of the light hydrocarbon separation column D, at 15 (oxygenate decomposition zone), the amount of alcohols in the light hydrocarbon stream 8 leaving the process can be reduced, because the water resulting from the decomposition of alcohols can be separated as free water from the overhead drum of the column D. This effect is particularly desired because in an optional dehydrogenation process the subsequent process steps typically require totally oxygen free feed. A still further possible location for the deoxygenation catalysts is at the bottom of light hydrocarbon separation column D, at 16 (oxygenate decomposition zone). At this location the catalyst is used for reducing the amount of oxygenates otherwise circulated back to the dimer separation column B.

In some cases it is advantageous to decompose traces of oxygenates in the light hydrocarbon effluent by placing the catalyst to the top of the light hydrocarbon separation column. For example, alcohols increase the acid consumption in alkylation and thus their amount in the light hydrocarbon separation column overhead should be minimized.

Figure 4:
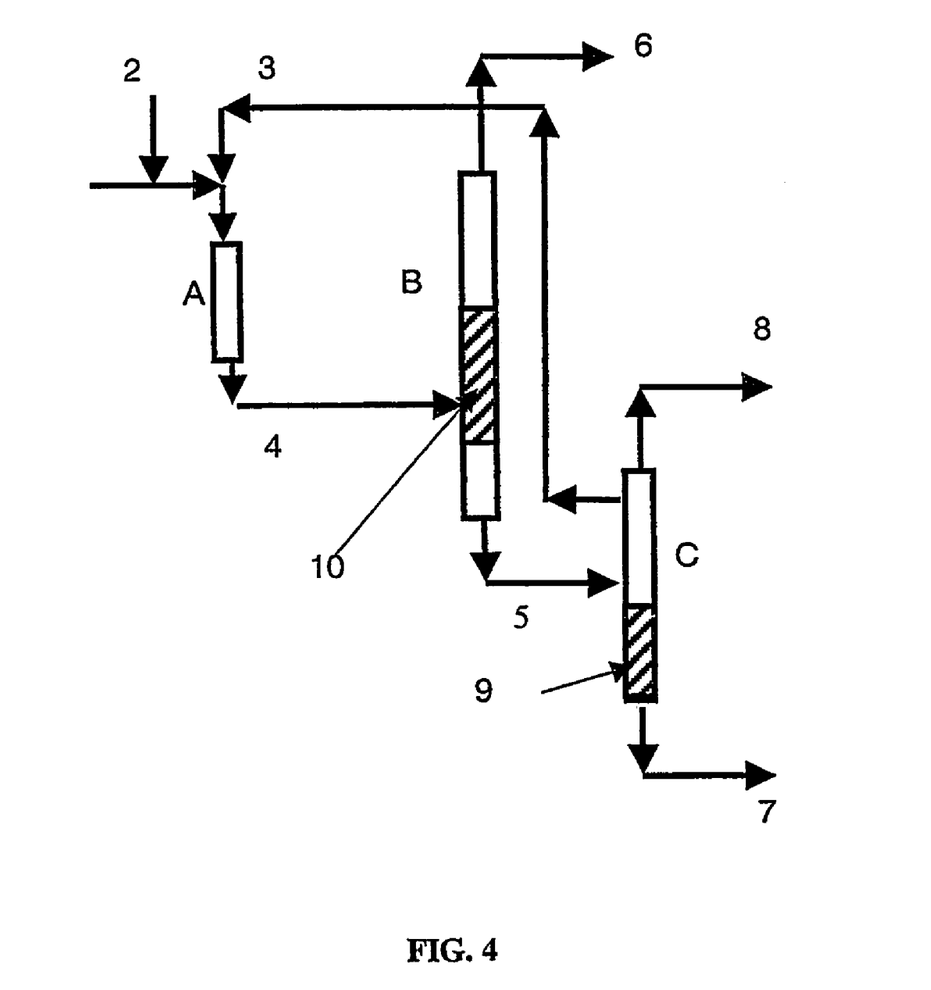
FIG. 4 represents an example of a process flow scheme suitable for a refinery C4 side stream used as dimerization feedstock.

In FIG. 4 an example of a process flow scheme suitable for refinery C4 side stream as dimerization feedstock is presented. There is only a single dimerization reaction zone A and the first column B (light hydrocarbon separation column) is used to separate the remaining light hydrocarbons from the dimer product. Hydrocarbon feed stream 1, oxygenate makeup stream 2 and the oxygenate rich recycle stream 3 are combined and fed to the dimerization reaction zone A. The effluent 4 from reaction zone A is conducted to the light hydrocarbon separation column B. Column B separates the remaining light hydrocarbons from the reactor effluent to stream 6. The bottom product of this column, stream 5, consists mainly of the produced dimers, higher oligomers, heavy oxygenate side products and optionally some light hydrocarbons. Stream 5 is conducted to second distillation column C, which performs the final separation to the dimer product 7 consisting mainly of the produced dimers, higher oligomers and heavy oxygenate side products. The intermediate boiling oxygenates are separated to the recycle stream 3 containing major portion of C4 and lighter alcohols present in the reactor effluent. The light hydrocarbons not removed in column B and C5-C6 hydrocarbons present in the feed can be recovered as an optional overhead stream 8. The dimer product 7 may be further conducted to hydrogenation step as described in the case of the process presented in FIGS. 1 and 3.

In this configuration the conditions at the lower end of the column C are near to those mentioned above in connection of the process for dimerizing dehydrogenation effluent. Preferably the catalyst is placed in the lower part 9 (oxygenate decomposition zone) of column C and a significant part of the released olefins can be returned to the dimerization section via recycle stream 3. When the catalyst is placed in column B (item 10), the olefins released from oxygenates end up in the leaving light hydrocarbon stream 6. In a typical case the light hydrocarbon stream 6 leaving the dimerization unit is treated in an alkylation unit for which olefins are suitable feed. However, in this arrangement part of the butanols used for the moderation of the dimerization reaction are decomposed as well and thus the amount of makeup water must be increased.

It is possible to configure the system such that oxygenates are decomposed almost completely to water and olefins in a distillation column. Such a process is presented schematically in FIG. 5. In this process hydrocarbon feed containing olefins, stream 1, is mixed with stream 2 comprising water, methanol, tert-butanol or some other oxygenate used for controlling the reaction selectivity, and fed to the dimerization reaction zone A. The dimerization reactor effluent of this reaction zone, stream 3 is conducted to distillation column B. This column is operated so that the dimer product and oligomer side products concentrate to the bottom product 5 of the column B and unreacted light hydrocarbons leave the process via the distillate 4 of this column. Because only light hydrocarbons are let out at the top and only dimers and heavier components are let out via the bottom, the intermediate boiling components, like butanols in the case of isobutene dimerization, enrich to the middle part of the column B (item 6). When the deoxygenation catalyst is placed there, oxygenates decompose to their constituents, light olefins and water leave the process with the distillate stream 5 or as free water from the condenser of the column.

Figure 5:
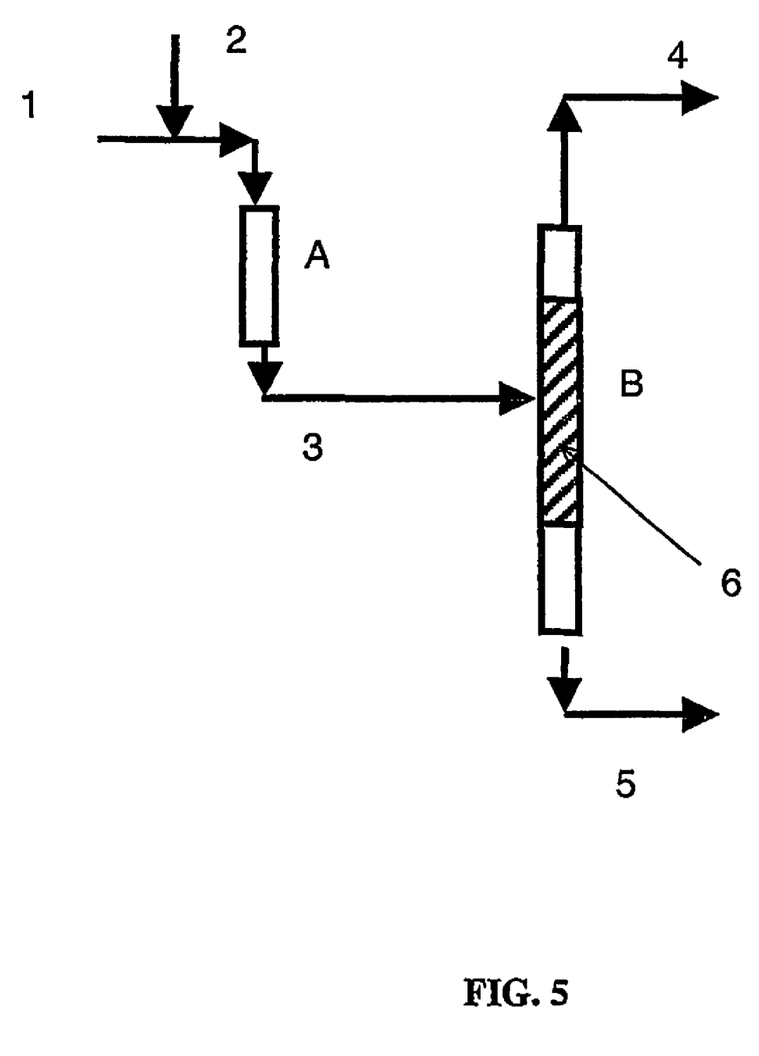
FIG. 5 represents a system wherein essentially all oxygenates present in the dimerization reactor effluent are decomposed in a distillation column, eliminating thereby the need of the oxygenate recycle.

In this arrangement, no additional oxygenate separation stage is necessary and the oxygenate recycle to the dimerization reaction section can be eliminated. The oxygenates present in the dimerization reactor effluent, comprising tertiary butanol or secondary butanol or tertiary amyl alcohol, are decomposed in the distillation column separating light unreacted hydrocarbons and dimer product from said reactor effluent.

Naturally if the purity requirements for the leaving streams are very high, this arrangement can be complemented by further purification steps such as wash stages or adsorption. Light hydrocarbons are understood as C1-C6 hydrocarbons.

Figure 6:
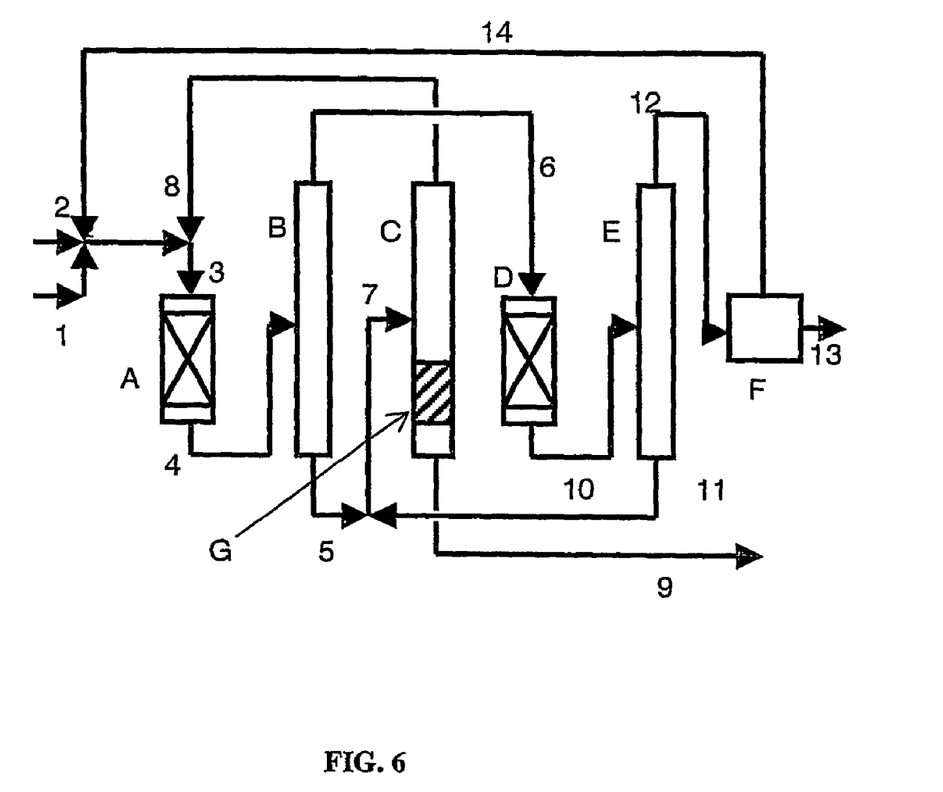
FIG. 6 presents schematically a system using primary alcohol as oxygenate similar to the one of FIG. 2, but additionally containing the features of the invention.

If the dimerization process is designed to use primary alcohol as oxygenate, like in the one disclosed in GB 2325237, both the process flow scheme and side products are different as explained above. The operation of the process was described in FIG. 2. FIG. 6 presents schematically such process flow unit. By placing a suitable catalyst capable of decomposing oxygenates, especially ethers, to the lower end of the dimer separation column C (item G), C9 ether can be converted back to methanol and isooctene, which is the desired product. Isooctene follows the bottom product and methanol can be recycled with other recycled component recovered as distillate. Thus the quality of the product is improved and methanol makeup rate can be reduced.

In some special cases it may be considered advantageous to place deoxygenation catalyst in some other places in the system e.g. in order to adjust the MTBE-methanol ratio in the reactor inlets. This can be accomplished by placing MTBE decomposing catalyst to the upper ends of columns B and C of FIG. 6 (not presented in the figure).

Figure 7:
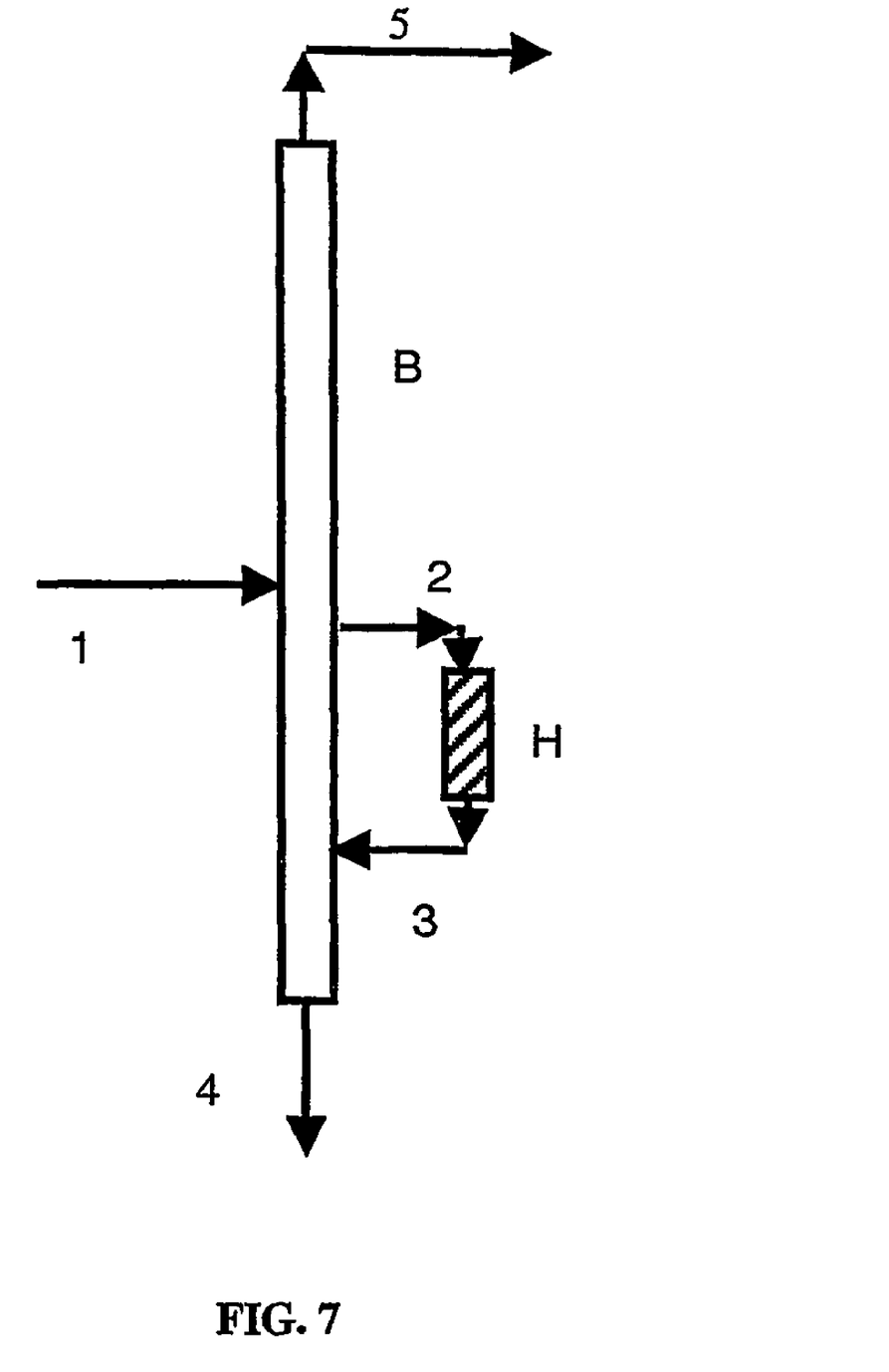
FIG. 7 illustrates an embodiment according to the invention wherein the catalyst is placed in an external vessel connected to a distillation column.

FIG. 7 illustrates an embodiment according to the invention wherein the deoxygenation catalyst is placed in an external vessel connected to a column. In FIG. 7 stream 1, which is an effluent from the dimerization reaction stage, is conducted to a distillation column B, from which a side stream 2 is conducted to a vessel H wherein a deoxygenation catalyst is located. From vessel H stream 3 is conducted to column B. Stream 3 can be returned to the column below or above the draw point. This figure represents a general arrangement, which can be used for replacing any of beds inside the columns in FIGS. 3-6.

It should be kept in mind that although the above presented examples are concentrated in C4 dimerization processes, simply because currently they are the most common ones, the same invention applies as well to dimerization of other olefins, particularly in the C2-C10 range. This invention can be applied equally well to the dimerization of isoamylenes or their codimerization with C3-C7 olefins. It is also evident to a man skilled in the art that the process can be optimized as necessary depending on the feedstock used and taking into account the suitable temperature range of the catalyst used.

As for the catalyst, the decomposition of oxygenates is accelerated typically by many sufficiently acidic catalysts. Because the process temperature is high and the conditions favor the decomposition, the necessary amount of catalyst is small. In some instances, excessive amount of catalyst may have even a negative impact by causing formation of heavier olefin oligomers.

In the following examples of suitable deoxygenation catalysts are presented.

Catalysts based on ion exchange resins made of sulfonated polyvinyl-divinylbenzene-copolymer can be used. Amberlyst® 15 and 35 are commercial examples of such resins. Halogenated variants of the previous ones, like fluorinated Nafion® resins can be used because of their good temperature stability. Their use in applications for decomposition of oxygenates is disclosed in U.S. Pat. No. 5,849,971 and U.S. Pat. No. 4,423,271.

Also less acidic catalysts, e.g. ion-exchange resins totally or partially neutralized with metal ions can be used for oxygenate decomposition as presented in U.S. Pat. No. 4,629, 710.

Other possible catalysts for oxygenate decomposition include inorganic salts impregnated with sulfonic acid groups as disclosed in U.S. Pat. No. 6,028,239, silica impregnated with alumina as disclosed in U.S. Pat. No. 5,043,519, or alumina silica catalyst as disclosed in U.S. Pat. No. 5,095, 164.

Minor amounts of sulfonic acid or mineral acids like sulfuric acid are very efficient as disclosed in EP 0 712 824. However, as being liquids they need continuous addition and special consideration in order to avoid corrosion problems.

Also various zeolites, such a type ZSM-5 have been successfully used for oxygenate decomposition.

In the dimer products of some dimerization processes according to the state of the art there may be 0.1 ... 5 weight % of ethers, alcohols, acids, ketones and the like and other oxygenates. This invention is also applicable for said processes.

A very remarkable benefit of the invention is that the light olefins, typically C3-C6 released from oxygenates are returned to the dimerization zone instead of remaining in the dimer product. Thus they can be converted to the desired dimer product instead of being used as fuel or remaining to the product as contaminants lowering its market value.

Oxygenates comprising C8-ethers or C9-ethers can be decomposed in a distillation column separating the dimer product with the catalyst placed in the distillation column or in a vessel connected to the column. Further, oxygenates comprising C4-alcohols or C5-alcohols can be decomposed in the distillation column separating the unreacted light hydrocarbons from the reactor effluent with catalyst placed in the distillation column or in a vessel connected to the column.

The oxygenates are removed from the dimer product and the from the light olefin fraction. The amount of oxygenates is significantly lower in the obtained dimer product when compared to products obtained using processes according to the state of the art.

As explained above it is especially useful to remove oxygenates from the dimer product if the dimer product is hydrogenated in a subsequent process stage. The product losses are reduced, less hydrogenation catalyst is needed and hydrogenation conditions can be milder. The goal can be achieved without adding major process devices to the dimerization plant, only a suitable catalyst needs to be introduced to suitable locations.

The invention claimed is:

1. A method for catalytic deoxygenation of process fluids of olefin dimerization processes, wherein at least part of olefin feed is dimerized and the product is separated, which process comprises:
    contacting at least one process fluid, containing oxygenates comprising C8-ethers or C-9 ethers, in an olefin dimerization process with an acidic deoxygenation catalyst in a section of a dimer separation column between the feed point and a reboiler;
    decomposing the oxygenates in the process fluid; and
    removing the oxygenates from the dimer product of the olefin dimerization process.

2. The method according to claim 1, wherein the process fluid containing oxygenates is brought into contact with the deoxygenation catalyst at thermodynamic conditions comprising a pressure range of 100-5000 kPa and temperature range of 30-300° C.

3. The method according to claim 1 or 2, wherein the oxygenates comprise n-butyl-tert-butylether, sec-butyl-tert-butylether, di-sec-butyl-butylether, tert-amylalcohol, methyl-tert-butyl-ether, methyl-sec-butyl-ether, ethyl-tert-butyl-ether, ethyl-sec-butyl-ether, methyl-iso-octyl-ether, ethyl-iso-octyl-ether, methyl-tert-amyl-ether and ethyl-tea-amyl-ether.

4. The method according to claim 1, wherein the temperature range is 150-220° C.

5. The method according to claim 1 or 2, wherein the acidic deoxygenation catalyst is an ion-exchange resin made of sulfonated polyvinyl-divinylbenzene copolymer, a halogenated variant thereof, an ion-exchange resin neutralized with metal ions, inorganic salt impregnated with sulfonic acid groups or a zeolite.

6. The method according to claim 3, wherein the acidic deoxygenation catalyst is an ion-exchange resin made of sulfonated polyvinyl-divinylbenzene copolymer, a halogenated variant thereof, an ion-exchange resin neutralized with metal ions, inorganic salt impregnated with sulfonic acid groups or a zeolite.

7. The method according to claim 4, wherein the acidic deoxygenation catalyst is an ion-exchange resin made of sulfonated polyvinyl-divinylbenzene copolymer, a halogenated variant thereof, an ion-exchange resin neutralized with metal ions, inorganic salt impregnated with sulfonic acid groups or a zeolite.

8. A method for catalytic deoxygenation of process fluids of olefin dimerization processes, wherein at least part of olefin feed is dimerized and the product is separated, which process comprises:
- contacting at least one process fluid containing oxygenates comprising C8-ethers or C-9 ethers in an olefin dimerization process with an acidic deoxygenation catalyst in a section of a dimer separation column between the feed point and a reboiler;
- decomposing the oxygenates in the process fluid; and
- removing the oxygenates from the dimer product of the olefin dimerization process,
- wherein the catalyst is placed at a predetermined location such that the concentration of the oxygenates present at said location is higher than the thermodynamic equilibrium concentration of the oxygenates to be decomposed.

* * * * *